United States Patent [19]

Godrej et al.

[11] Patent Number: 5,298,247
[45] Date of Patent: Mar. 29, 1994

[54] NEEM OIL FATTY ACID DISTILLATION RESIDUE BASED PESTICIDE

[75] Inventors: Nadir B. Godrej; Keki B. Mistry; Brahmanand A. Vyas, all of Bombay, India

[73] Assignee: Godrej Soaps Limited, Bombay, India

[21] Appl. No.: 879,606

[22] Filed: May 7, 1992

[51] Int. Cl.$^5$ .................. A61K 35/78; A61K 31/35
[52] U.S. Cl. .................. 424/195.1; 514/453
[58] Field of Search .................. 424/195.1; 514/453

[56] References Cited

U.S. PATENT DOCUMENTS

| | | | |
|---|---|---|---|
| 4,556,562 | 12/1985 | Larsen | 424/195.1 |
| 4,902,713 | 2/1990 | Rembold et al. | 514/453 |
| 4,946,681 | 8/1990 | Walter | 424/195.1 |
| 5,001,146 | 3/1991 | Carter et al. | 514/453 |
| 5,110,591 | 5/1992 | Williams | 424/195.1 |
| 5,124,349 | 6/1992 | Carter et al. | 514/453 |

OTHER PUBLICATIONS

"Potential of the Neem Tree (Azadirachta indica) for Pest Control and Rural Development"–Authors: Saleem Ahmed and Michael Grainge.

"Utilization of Non-edible Oilseeds-Recent Trends"–Authors: O. P. Vimal and K. T. Naphade.

*Primary Examiner*—John W. Rollins
*Attorney, Agent, or Firm*—Ladas & Parry

[57] ABSTRACT

Neem oil fatty acid distillation residue based pesticide which is storage stable, water soluble, environmentally safe and rich in bitter principles. It is obtained by saponifying the neem oil fatty acid distillation residue with an aqueous alkali, drying the resulting soap, allowing the resulting soap cake to cool down to room temperature, pulverising the soap cake, fortifying the resulting fines by mixing with a small quantity of neem oil, allowing the fines to dry at room temperature and if desired, forming an aqueous emulsion by mixing the pesticidal fines with water at room temperature. The fines may be enriched by mixing with a small quantity of a solvent extract of neem tree parts prior to allowing the fines to dry.

11 Claims, No Drawings

NEEM OIL FATTY ACID DISTILLATION RESIDUE BASED PESTICIDE

This invention relates to neem oil fatty acid distillation residue based pesticide and a process for the preparation thereof.

Pesticides of plant origin are in general preferable to the synthetic ones because of their relatively shorter persistance in the atmosphere, easier biodegradability and lower toxicity to human beings and other flora and fauna.

Neem oil from neem tree (*Azadirachta indica*) is known to possess pesticidal activity. Direct spraying of neem oil on plants is likely to result in deposition of high concentration of oil on the foliage of plants. This will be toxic and harmful to the foliage of plants, besides being uneconomical. Therefore, from the economic and toxicity points of view, neem oil has to be mixed with water to spray on foliage and plants, but aqueous emulsion of neem oil is not known to have been used on a commercial scale as a pesticide due to factors such as cost of high concentration of neem oil required in the emulsion for effective pest control, unstable nature of the aqueous emulsion over long periods of time and phutotoxic symptoms on the foliage and plants.

The limonoid bitter principles (lipid associates) such as azadirachtin, salanin, meliantriol, deacetylsalanin and nimbidin contained in the neem oil are reported to be responsible for the pesticidal activity of neem oil. (Vimal, O.P. and Naphade, K.T. 1980, Jour. Sci. Ind. Res. Vol. 39, p. 197-211).

U.S. Pat. No. 4,556,562 (1985) of Robert O Larson describes a process for the preparation of a storage stable aqueous emulsion of neem seed extract consisting of forming neem seed particles, extracting the particles with ethanol at 60° C. to 90° C. and separating the extract to obtain a solution of 40 to 45% by weight of neem oil containing azadirachtin and diluting the solution with water and non-ionic emulsifying agent to form an aqueous emulsion and if necessary adjusting the pH of the emulsion between 3.5 to 6.0 with ammonium hydroxide.

Neem oil fatty acid distillation residue is a byproduct formed during fractional distillation of fatty acids obtained by hydrolysis (high pressure splitting) of neutral neem oil at 380 to 400 psi (pounds per square inch) pressure and 230° to 240° C. The neutral neem oil is obtained by distillative deacidification of industrial grade neem oil. Neem oil fatty acid distillation residue is a thick dark brown viscous liquid insoluble in water. Because of the thick viscous nature of the residue it also can not be normally formed into an aqueous emulsion thereof as such. It may be obvious to an oil technologist that an aqueous emulsion of the residue could however, be made by dissolving the residue in an organic solvent with an emulsifier and diluting the emulsifiable concentrate with water. An organic solvent based aqueous emulsion of the residue is not reported to have been neither made nor used as a pesticide. To the best of our knowledge, neem oil fatty acid distillation residue is of no or negligible commercial value and is disposed of as a waste material or used as fuel in furnaces.

By extensive research and experiments we have found out a neem oil fatty acid distillation residue based pesticide which is storage stable, water soluble, environmentally safe and rich in bitter principles.

An object of the present invention is to provide a neem oil fatty acid distillation residue based pesticide which is storage stable, water soluble, environmentally safe and rich in bitter principles.

Another object of the present invention is to provide a process for the preparation of the neem oil fatty acid distillation residue based pesticide.

The process for the preparation of the neem oil fatty acid distillation residue based pesticide consists of:
i) saponifying the neem oil fatty acid distillation residue with an aqueous alkali at 85° to 140° C. and atmospheric pressure, the concentration of the alkali in water being 10 to 50% by weight and the molar ratio of the residue and alkali being 1:1.05 to 1:1.2;
ii) drying the resulting soap at 100°-110° C.;
iii) allowing the resulting soap cake to cool down to room temperature;
iv) pulverising the soap cake;
v) fortifying the resulting fines by mixing with 5 to 10% by weight of neem oil;
vi) allowing the fines to dry at room temperature and obtain the pesticide; and
vii) if desired forming an aqueous emulsion of the pesticide by mixing the pesticidal fines with water at room temperature in the ratio 0.5:100 to 3:100.

The alkali used for saponification of step (i) is, for example, sodium or potassium hydroxide, sodium hydroxide being the preferred alkali as it results in harder soap which can be converted into fines easily.

A concentrated alkali solution containing 45 to 50% by weight of the sodium hydroxide is preferred for the saponification of step (i) as the resulting soap will have reduced water content and can be dried faster.

A dilute aqueous alkali solution containing as low as 2% by weight of alkali concentration could also be used for saponification of step (i) but the resultant soap would contain a lot of moisture and require additional energy for drying. A dilute aqueous alkali (containing as low as 2% by weight of alkali concentration) saponification is also, however, within the scope of the present invention and its scope should be construed accordingly.

The saponification of step (i) is preferably, carried out at 90° C.

The molar ratio of the residue and alkali for the saponification of step (i) is, preferably 1:1.1 to 1:1.2.

The soap cake is pulverised as per step (iv) into fines of 1.0 to 1.4 mm, preferably 1.1 to 1.2 mm size particles.

The fortification of the fines with neem oil as per step (v) has been found to prevent caking of the fines and increase the shelf life of the pesticide and also fortify the pesticide with the bitter principles some of which may have been lost or may have undergone chemical changes partially or fully during the high pressure splitting of the neutral neem oil.

An emulsion of the pesticide as per step (vii) is formed by mixing the pesticide fines with water at room temperature in the ratio 0.5:100 to 3:100 (w/w) at the time of spraying of the pesticide on the foliage of plants. A concentration of 0.5% to 3.0% by weight of the pesticide was found to be quite effective as can be seem from the following tables.

In order to enrich the fines obtained by step (v) with the bitter principles, the fines may be mixed with 5 to 10% of a solvent extract of neem tree parts such as seeds, leaves, or barks prior to allowing the fines to dry as per step (vi). The solvent extract is prepared in known manner using a solvent such as methanol, ethanol, acetone or petroleum ether.

Preferably, the soap is dried as per step (ii) at 110° C.

The following examples are illustrative of the present invention but not limitative of the scope thereof.

EXAMPLE 1

Neem oil fatty acid distillation residue (1 kg) was heated to 90° C. in a sigma mixer at atmospheric pressure and a solution of sodium hydroxide (107 g; 2.6 moles) in water (100 milliliters) was added to it under stirring over one hour. The soap was dried in an electric oven at 110° C. for 4 hours. The soap cake was allowed to cool down to room temperature and contained a moisture content of 1%. The cake was pulverised in a hammer type pulveriser into fines of 1.1 to 1.2 mm. The fines (1.0 kg) were mixed with industrial grade neem oil (50 g) and allowed to dry at room temperature. The pesticidal fines were dark brown and completely free flowing.

EXAMPLE 2

The procedure of example 1 was followed and the fines mixed with neem oil were further mixed with methanol extract of neem seeds (50 milli liters) prior to drying at room temperature. The pesticidal fines were dark brown and completely free flowing.

The methanol extract was prepared as follows:

Neem seeds (50 g) containing 18% by weight of neem oil were crushed and soaked in methanol (50 ml) for 4 hours under stirring at room temperature. The seed particles were separated from the methanol extract and extracted twice again with fresh methanol (25 ml) for 15 minutes each time. The methanol extracts were pooled together.

Using aqueous emulsions of the pesticide of examples 1 and 2, bioefficacy (pesticidal activity) studies were carried out and the results are shown in the following tables. The aqueous emulsions were prepared by mixing the pesticide of examples 1 and 2 in water at room temperature.

The following tables 1 to 3 give test results in laboratory:

TABLE 1

Bioefficacy of the aqueous emulsion of the pesticide of example 1 on the food consumption by larvae of tobacco caterpillar (*Spodoptera litura*)

| | % Feeding | | | | Pupal |
|---|---|---|---|---|---|
| | Larval stages | | | | |
| Treatments | IInd | IIIrd | IVth | Vth | Wt (mg) |
| Control (Water) | 5.7 ± 1.3 | 7.1 ± 1.1 | 12.5 ± 1.0 | 13.1 ± 2.1 | 379 ± .03 |
| Percentage of the pesticide of example 1 in the aqueous emulsion thereof | | | | | |
| (0.5%) | 3.4 ± 0.7 | 4.7 ± 0.5 | 5.3 ± 0.8 | 8.7 ± 1.9 | 293 ± .03 |
| (1.0%) | 3.4 ± 1.1 | 4.0 ± 0.6 | 4.6 ± 0.2 | 8.2 ± 1.0 | 262 ± .02 |
| (2.0%) | 3.0 ± 0.9 | 3.7 ± 0.5 | 4.5 ± 0.9 | 6.3 ± 0.6 | 256 ± .02 |
| (3.0%) | 2.1 ± 1.2 | 3.0 ± 1.0 | 4.0 ± 0.4 | 6.0 ± 0.5 | 234 ± .01 |

$$\% \text{ Feeding} = \frac{\text{Leaf area offered for feeding} - \text{Leaf area left}}{\text{Leaf area offered for feeding}} \times 100$$

TABLE 2

Bioefficacy of the aqueous emulsion of the pesticide of example 1 on pod borer/fruit borer (*Heliothis armigera*)

| Treatments | | % Mortality* | | | | | | |
|---|---|---|---|---|---|---|---|---|
| Stages | | Larva | | Pre pupa | | | Pupa | |
| Days after hatching→ | | 9 | 10 | 13 | 14 | 16 | 17 | 25 |
| Control (Water) | (0.5%) | 12.8 | 28.5 | 28.5 | 21.5 | 72.4 | 72.4 | 100.00 |
| Percentage of the pesticide of example 1 in the aqueous emulsion thereof | (1.0%) | 42.0 | 71.0 | 100.0 | 100.0 | 100.0 | 100.0 | 100.0 |

$$^*\text{Corrected mortality} = \frac{\% \text{ Alive in control} - \% \text{ Alive in treated}}{\% \text{ Alive in control}} \times 100$$

TABLE 3

Bioefficacy of the aqueous emulsion of the pesticide of example 1 on spotted boll worm (*Earias vitella*)

| Treatments | No of days larva alive after treatment | Days taken for pupation | Pupal Duration (days) | Pupal Wt (g) |
|---|---|---|---|---|
| Control (Water) | 6.7 ± 0.27 | 5.7 ± 0.28 | 7.8 ± 0.21 | 0.055 ± 0.00 |
| Percentage of the pesticide of example 1 in the aqueous emulsion thereof | | | | |
| (0.5%) | 3.9 ± 0.25 | 5.0 ± 0.10 | 10.0 ± 0.00 | 0.045 ± 0.01 |
| (1.0%) | 3.9 ± 0.29 | 6.3 ± 0.10 | 12.0 ± 0.19 | 0.042 ± 0.01 |
| (2.0%) | 3.8 ± 0.18 | 6.5 ± 0.08 | 12.0 ± 0.00 | 0.040 ± 0.01 |
| (3.0%) | 3.2 ± 0.12 | 8.0 ± 0.00 | No adult | 0.030 ± 0.00 |

TABLE 3-continued

Bioefficacy of the aqueous emulsion of the pesticide of example 1 on spotted boll worm (*Earias vitella*)

| Treatments | No of days larva alive after treatment | Days taken for pupation | Pupal Duration (days) | Pupal Wt (g) |
|---|---|---|---|---|
| | | | emergence | |

Each value is the mean of 20 replicates ± standard error of means.

The following tables 4 to 10 give test results obtained under field conditions

TABLE 4

Bioefficacy of the aqueous emulsion of the pesticide of example 1 on the incidence of Aphids (*Aphis gossypii*) on Cotton at Phaltan, District Satara, Maharashtra, India
Number of sprays = 4, each at an interval of 15 days
Concentration of the pesticide of example 1, 1 Kg/acre in 200 liters of water (0.5%).

| Date of observation | Insect count* | | |
|---|---|---|---|
| | Water spray control | The pesticide of example 1 | Critical Difference (p = 0.05) |
| 17.6.88 (Precount) | 40.6 | 41.6 | n.s. |
| 18.6.88 | SECOND SPRAY | | |
| 19.6.88 | 31.3 | 21.3 | 7.527 |
| 20.6.88 | 37.3 | 19.3 | 7.918 |
| 23.6.88 | 42.6 | 21.6 | 10.261 |
| 28.6.88 | 49.0 | 27.6 | 10.690 |
| 03.7.88 | 55.3 | 32.6 | 10.925 |
| Average | 43.1 | 24.48 | |
| 03.7.88 | THIRD SPRAY | | |
| 04.7.88 | 40.3 | 23.0 | 10.177 |
| 05.7.88 | 47.6 | 20.3 | 11.537 |
| 08.7.88 | 55.3 | 30.3 | 11.928 |
| 13.7.88 | 60.0 | 21.3 | 12.194 |
| 18.7.88 | 64.0 | 27.3 | 13.610 |
| Average | 53.4 | 24.44 | |
| 18.7.88 | FOURTH SPRAY | | |
| 19.7.88 | 40.0 | 25.0 | 12.527 |
| 20.7.88 | 42.3 | 20.0 | 12.411 |
| 23.7.88 | 47.6 | 16.6 | 12.476 |
| 28.7.88 | 52.3 | 21.3 | 13.190 |
| 02.8.88 | 55.6 | 24.3 | 13.452 |
| Average | 47.5 | 21.44 | |

*Number of aphids on 5 randomly selected plants in each plot

TABLE 5

Bioefficacy of the aqueous emulsion of the pesticide of example 1 on the incidence of Jassids (*Amrasca biguttula*) on Okra at Phaltan, District Satara, Maharashtra, India
Number of sprays = 3, each at an interval of 15 days
concentration of pesticides of example 1
1 Kg/acre in 200 liters water (0.5%)

| Date of observation | Insect count* | | |
|---|---|---|---|
| | Water spray control | Pesticide of example 1 | Critical Difference (p = 0.05) |
| 01.1.89 (Precount) | 28.25 | 27.25 | n.s. |
| | FIRST SPRAY | | |
| 02.1.89 | 24.25 | 20.25 | 3.021 |
| 03.1.89 | 30.25 | 15.25 | 3.628 |
| 06.1.89 | 31.00 | 16.00 | 3.909 |
| 11.1.89 | 34.25 | 17.00 | 4.611 |
| 16.1.89 | 40.25 | 17.00 | 5.011 |
| Average | 32.00 | 17.10 | |
| | SECOND SPRAY | | |
| 17.1.89 | 30.00 | 16.25 | 5.621 |
| 18.1.89 | 32.00 | 16.25 | 6.711 |
| 21.1.89 | 32.25 | 15.00 | 6.952 |
| 26.1.89 | 37.25 | 15.00 | 7.811 |
| 31.1.89 | 40.25 | 15.50 | 7.921 |
| Average | 34.35 | 15.60 | |
| | THIRD SPRAY | | |
| 01.2.89 | 30.00 | 11.25 | 8.511 |
| 02.2.89 | 32.25 | 11.00 | 8.942 |
| 05.2.89 | 37.25 | 16.25 | 8.723 |
| 10.2.89 | 40.50 | 12.00 | 9.162 |
| 15.2.89 | 46.25 | 12.00 | 9.513 |
| Average | 37.25 | 12.50 | |

*Number of Jassids on 5 randomly selected plants in each plot

TABLE 6

Bioefficacy of the aqueous emulsion of the pesticide of example 1 on Cotton boll damage and the yield of seed cotton at Phaltan, District Satara, Maharashtra, India
Total number of sprays = 4, each at an interval of 15 days
Concentration of the pesticide of example 1 kg/acre in 200 liters water (0.5%)

| Treatments | % bud damage due to *Earias vitella* (spotted boll worm) | % boll damage due to *Pectinophora gossypiella* (Pink boll worm) | Seed Cotton yield Q/ha* |
|---|---|---|---|
| Water sprayed control | 40.8 | 32.6 | 7.62 |
| Aqueous emulsion of the pesticide of example 1 | 35.8 | 30.2 | 10.68 |
| % change over control with the aqueous emulsion of the pesticide of example 1 | (−12.2) | (−7.3) | (+40.1) |

*Q/ha = Quintals/Hectare
No phytotoxic symptoms were recorded in any plot.

TABLE 7

Bioefficacy of the aqueous emulsion of the pesticide of example 1 on the fruit damage and yield of Okra at Phaltan, District Satara, Maharashtra, India
Total number of sprays = 3, each at an interval of 15 days
Concentration of the pesticide of example 1 - 1 Kg/acre in 200 liters water (0.5%)

| Treatments | % fruit damage due to *Earias Vitella* | Green fruit yield (Quintals/Hectare) |
| --- | --- | --- |
| Water sprayed control | 47.38 | 21.20 |
| Aqueous emulsion of the pesticide of example 1 | 28.64 | 26.68 |
| % change over control | (−39.55) | (+25.85) |

TABLE 7-continued

Bioefficacy of the aqueous emulsion of the pesticide of example 1 on the fruit damage and yield of Okra at Phaltan, District Satara, Maharashtra, India
Total number of sprays = 3, each at an interval of 15 days
Concentration of the pesticide of example 1 - 1 Kg/acre in 200 liters water (0.5%)

| Treatments | % fruit damage due to *Earias Vitella* | Green fruit yield (Quintals/Hectare) |
| --- | --- | --- |
| with the aqueous emulsion of the pesticide of example 1 | | |

No phytotoxic symptoms were recorded in any plot.

TABLE 8

Bioefficacy of the aqueous emulsion of the pesticide of examples 1 and 2 on the infestation of cabbage aphids (*Bravicoryne brassicae*) in cabbage at Phaltan, District Satara, Maharashtra, India
Total number of sprays = 3, each at an interval of 15 days
Concentration of the pesticide of examples 1 and 2, 1 kg/acre 200 liters water (0.5%)

| Date of observation | Water sprayed Control | Aqueous emulsion of the pesticide of example 1 | Aqueous emulsion of the pesticide of example 2 | Critical Difference ($p = 0.05$) |
| --- | --- | --- | --- | --- |
| 11.1.90 Precount | 63.33 | 66.0 | 68.66 | 2.22 |
| 12.1.90 | | First Spray | | |
| 13.1.90 | 59.66 | 34.33 | 30.33 | 2.46 |
| 14.1.90 | 60.33 | 29.33 | 24.33 | 2.06 |
| 17.1.90 | 62.66 | 32.33 | 20.66 | 1.93 |
| 22.1.90 | 69.00 | 35.00 | 27.33 | 1.65 |
| 27.1.90 | 74.33 | 40.66 | 28.66 | 1.29 |
| Average | 65.19 | 34.33 | 26.26 | |
| 29.1.90 | | Second Spray | | |
| 30.1.90 | 66.66 | 20.33 | 17.33 | 1.21 |
| 31.1.90 | 67.66 | 20.33 | 18.00 | 1.53 |
| 03.2.90 | 74.33 | 18.33 | 14.66 | 1.37 |
| 07.2.90 | 77.66 | 26.66 | 22.66 | 1.62 |
| Average | 71.58 | 21.44 | 18.16 | |
| 7.2.90 | | Third Spray | | |
| 8.2.90 | 80.33 | 18.33 | 16.00 | 1.57 |
| 9.2.90 | 85.66 | 17.00 | 15.33 | 1.28 |
| 12.2.90 | 89.33 | 18.66 | 16.33 | 1.21 |
| 17.2.90 | 92.33 | 22.33 | 20.33 | 1.11 |
| 22.2.90 | 114.0 | 35.66 | 30.33 | 1.15 |
| Average | 92.33 | 22.39 | 19.66 | |

*Number of aphids counted on 5 randomly selected plants in each plot.

TABLE 9

Bioefficacy of the aqueous emulsion of the pesticide of examples 1 and 2 on the infestation of Diamond back moth larvae (*Plutella maculepennis*) of Cabbage at Phaltan, District Satara, Maharashtra, India
Total number of sprays = 3, each at an interval of 15 days
Concentration of the pesticide of examples 1 and 2, 1 Kg/acre in 200 liters water (0.5%)

| Date of observation | Water sprayed Control | Aqueous emulsion of the pesticide of the example 1 | Aqueous emulsion of the pesticide of example 2 | Critical Difference ($p = 0.05$) |
| --- | --- | --- | --- | --- |
| 28.1.90 Precount | 21.33 | 24.33 | 22.66 | 1.86 |
| 29.1.90 | | Second spray | | |
| 30.1.90 | 24.00 | 15.00 | 15.66 | 1.92 |
| 31.1.90 | 23.66 | 15.00 | 15.00 | 1.80 |
| 3.2.90 | 32.66 | 16.33 | 16.33 | 2.86 |
| 7.2.90 | 37.66 | 17.00 | 17.66 | 2.11 |
| Average | 29.49 | 15.83 | 16.16 | |
| 7.2.90 | | Third spray | | |
| 8.2.90 | 40.00 | 14.33 | 11.00 | 2.06 |
| 9.2.90 | 41.66 | 14.33 | 14.33 | 2.53 |
| 12.2.90 | 47.00 | 18.00 | 14.66 | 2.76 |
| 17.2.90 | 48.33 | 18.33 | 16.33 | 2.13 |
| 22.2.90 | 53.66 | 20.33 | 17.00 | 2.06 |
| Average | 46.16 | 17.04 | 14.66 | |

*Numbers of Diamond-back moth larvae counted on 5 randomly selected plants in each plot.

TABLE 10

Bioefficacy of the aqueous emulsion of the pesticide of example 1 vis-a-vis different neem extracts on the infestation of pod borer (*Heliothis armigera*) and yield of gram (*cicer arietinum*) at Banswara, Rajasthan, India

| Treatments | Pod damage % | Seed Yield (Quintals/Hectare) |
|---|---|---|
| Control (water spray) | 27.55 | 7.65 |
| Aqueous suspension of neem seed extract (5% concentration in water) | 17.04 | 8.65 |
| Aqueous suspension of neem leaves extract (5% concentration in water) | 15.86 | 8.30 |
| Aqueous suspension of neem oil fatty acid distillation residue dissolved in benzene with polysorbate-80 (polyoxyethyle sorbitanmonooleate of HiCO Products Ltd., Bombay, India) (suspension concentration in water 5.0%) | 14.94 | 9.42 |
| Aqueous suspension of the pesticide of example 1 (0.5% concentration in water) | 10.55 | 12.69 |
| Critical Difference (p = 0.05) | 2.41 | 0.44 |
| % change over control with the aqueous emulsion of the pesticide of example 1 | −61.70 | +65.88 |

The tables 1 to 10 clearly establish the antifeedant, repellant and growth retardant activities of the pesticide of examples 1 and 2. The tables 5 and 10 also clearly establish that the aphids and jassids which have sucking type of mouth parts are controlled by the pesticide of the present invention indicated the systemic action of the pesticide, that the pesticide is translocated in the plant systems.

Neem products are reported to be very safe from the environmental point of view. There is very little persistence of neem products in soil, water and plants (Ahmad, S. and Grainge, M. 1986, Economic Botany, Vol. 40, p. 201-209). Neem tree parts such as leaves, fruits, stem, bark or roots are also known to be used in ayurvedic medicines from ancient times. It is, therefore, logical to conclude that the pesticide of the present invention is environmentally safe and is non toxic to human beings and other flora and fauna. Toxicity studies were, however, carried out using the aqueous emulsion of the pesticide of examples 1 and 2 and the results are given hereinbelow:

TABLE 11

Acute Oral Toxicity in rats

| | Dose mg/kg | % Mortality observation up to 7 days |
|---|---|---|
| 1 | Pelleted food without pesticide of example 2 (control) | 0 |
| 2 | Pelleted food + 2500 mg pesticide of example 2 | 0 |
| 3 | Pelleted food + 5000 mg pesticide of example 2 | 0 |
| 4 | Pelleted food + 7500 mg pesticide of example 2 | 0 |
| 5 | Pelleted food + 10000 mg pesticide of example 2 | 0 |

Animals appeared normal. Since there was no mortality, LD 50 value could not be determined.

TABLE 12

Acute dermal toxicity in rabbits

| | Dose mg/kg | % Mortality observation up to 7 days |
|---|---|---|
| 1 | Application of only saline on body (control) | 0 |
| 2 | Application of 5000 mg pesticide of example 2 moistened with saline | 0 |
| 3 | Application of 7500 mg pesticide of example 2 moistened with saline | 0 |
| 4 | Application of 10000 mg pesticide of example 2 moistened with saline | 0 |
| 5 | Application of 15000 mg pesticide of example 2 moistened with saline | 0 |

Animals appeared normal. Since there was no mortality, LD 50 values could not be determined. Visual postmortem report on the animals did not give any significant observation regarding toxicity.

TABLE 13

Toxicity study on *Talapia mossambica*, a fresh water fish

| | Dose (ppm) in water | % Mortality at the end of 96 hours |
|---|---|---|
| 1 | Water (control) No pesticide | 0 |
| 2 | 10 ppm concentration of pesticide of example 2 | 0 |
| 3 | 20 ppm concentration of pesticide of example 2 | 20 |
| 4 | 25 ppm concentration pesticide of example 2 | 40 |
| 5 | 30 ppm concentration pesticide of example 2 | 80 |
| 6 | 40 ppm concentration of pesticide of example 2 | 100 |

The LC 50 values calculated after 96 hours observation by graphical interpolation was found to be 27 ppm for the aqueous emulsion of the pesticide of example 2.

Mucous membrane irritation study in rabbits using the aqueous emulsion of the pesticide of example 2 (0.5%) showed mild irritation to the vaginal mucous membrane when compared to control (water).

The documented toxicity levels for pyrethrin, a pesticide of natural origin, are as follows:

a) Acute oral LD 50 far rats: 584–900 mg/kg body weight b) Acute percutaneous (dermal) LD 50 for rabbits: 1500 mg/kg body weight.

c) Pyrethrins are highly toxic to fish.

A comparison of the toxicity levels of pyrethrin mentioned above with the data of toxicity studies on aqueous emulsion of the pesticide of example 2 clearly shows that the aqueous emulsion of the pesticide of example 2 has negligible toxicity effects.

What is claimed is:

1. A process for the preparation of neem oil fatty acid distillation residue based pesticide consisting of:
   i) saponifying neem oil fatty acid distillation reside with an aqueous alkali at 85°–140° C. and atmospheric pressure, the alkali in water having a concentration of 10 to 50% by weight and the molar ratio of the residue and alkali being 1:1.05 to 1:1.2;
   ii) drying the resulting soap cake at 100°–100° C.;
   iii) allowing the resulting soap cake to cool down to room temperature;

iv) pulverizing the soap cake to produce fines;
v) fortifying the resulting fines by mixing with 5 to 10% by weight of neem oil; and
vi) allowing the fines to dry at room temperature and obtain the pesticide.

2. A process as claimed in claim 1, which further consists of enriching the fines obtained by step (v) by mixing the fines with 5 to 10% by weight of a solvent extract of neem tree parts prior to allowing the fines to dry as per step vi.

3. A process as described in claim 2, wherein the saponification as per step (i) is carried out with sodium hydroxide.

4. A process as claimed in claim 2, wherein the saponification as per step (i) is carried out with concentrated alkali containing 45 to 50% by weight of the alkali concentration.

5. A process as claimed in claim 2, wherein the saponification as per step (i) is carried out at 90° C.

6. A process as claimed in claim 2 wherein the molar ratio of the residue and alkali for the saponification of step (i) is 1:1.1 to 1:1.2.

7. A process as claimed in claim 2 wherein the soap cake is dried as per step (ii) at 110° C.

8. A process for the preparation of neem oil fatty acid distillation residue based pesticide as claimed in claim 2, further comprising the step of forming an aqueous emulsion of the pesticide by mixing the pesticidal fines with water at room temperature in the ratio 0.5:100 to 3:100.

9. A process for the preparation of neem oil fatty acid distillation residue based pesticide as claimed in claim 1, further comprising the step of forming an aqueous emulsion of the pesticide by mixing the pesticidal fines with water at room temperature in the ratio 0.5:100 to 3:100.

10. Neem oil fatty acid distillation residue based pesticide obtained by the process as claimed in claim 1.

11. Neem oil fatty acid distillation residue based pesticide obtained by the process as claimed in claim 2.